US010451558B1

(12) United States Patent  
Chenvert (10) Patent No.: US 10,451,558 B1  
(45) Date of Patent: Oct. 22, 2019

(54) VEHICLE LIGHTING

(71) Applicant: DENT IMPRESSIONS, INC., Rogers, MN (US)

(72) Inventor: Brian J. Chenvert, Rogers, MN (US)

(73) Assignee: Dent Impressions, Inc., Rogers, MN (US)

( * ) Notice: Subject to any disclaimer, the term of this patent is extended or adjusted under 35 U.S.C. 154(b) by 0 days.

(21) Appl. No.: 15/941,530

(22) Filed: Mar. 30, 2018

(51) Int. Cl.
G01N 21/88 (2006.01)
F21V 8/00 (2006.01)
G02B 1/04 (2006.01)
G01B 11/30 (2006.01)

(52) U.S. Cl.
CPC ....... *G01N 21/8806* (2013.01); *G01B 11/306* (2013.01); *G01N 21/8803* (2013.01); *G02B 1/045* (2013.01); *G02B 6/0043* (2013.01); *G02B 6/0051* (2013.01); *G02B 6/0055* (2013.01); *G02B 6/0058* (2013.01); *G01N 2021/8812* (2013.01); *G01N 2201/0634* (2013.01); *G01N 2201/0638* (2013.01)

(58) Field of Classification Search
CPC ........... G01N 21/8806; G01N 21/8803; G01N 2021/8812; G01N 2201/0634; G01N 2201/0638; G01B 11/306; G02B 1/045; G02B 6/0043; G02B 6/0051; G02B 6/0055; G02B 6/0058
See application file for complete search history.

(56) References Cited

U.S. PATENT DOCUMENTS

| 5,890,793 | A | 4/1999 | Stephens | |
| 8,256,084 | B1 * | 9/2012 | Bishop | H05K 3/1225 29/402.01 |
| 9,291,337 | B1 * | 3/2016 | Hulett | B23Q 17/2404 |
| 2007/0147760 | A1 * | 6/2007 | Iimura | G02B 6/0018 385/129 |
| 2015/0360271 | A1 | 12/2015 | Hawkins et al. | |
| 2016/0169462 | A1 * | 6/2016 | Hawkins | G01N 21/8806 362/219 |

* cited by examiner

*Primary Examiner* — Mary Ellen Bowman
(74) *Attorney, Agent, or Firm* — Brooks, Cameron & Huebsch, PLLC (57) ABSTRACT

A vehicle lighting apparatus may include a backing panel. The vehicle lighting apparatus may include a light guide panel (LGP) layered over the backing panel, wherein the LGP includes a front surface, a rear surface opposite the front surface, and a plurality of side surfaces connecting the front surface with the rear surface. The vehicle lighting apparatus may include a light source positioned along a first side surface of the plurality of side surfaces of the LGP. The vehicle lighting apparatus may include a front film layered over the front surface of the LGP, wherein the LGP includes a plurality of refraction elements that refract light emitted from the light source through the front surface of the LGP and through the front film and wherein a distribution pattern of the refraction elements creates a corresponding pattern of differing light intensities visible through the front film when illuminated by the light source.

20 Claims, 5 Drawing Sheets

VEHICLE LIGHTING

BACKGROUND

In addition to the functionality of a motor vehicle, consumers value the aesthetic of vehicles. Vehicles may receive damage such as dents or other surface deformities that degrade the appearance of the vehicle. Entire industries exist to create, maintain, and restore the appearance of vehicles. Properly identifying the deformities can assist in prescribing and/or performing a course of repair for the deformity. Particular lighting conditions may assist in properly identifying the deformities.

DETAILED DESCRIPTION

The process of identifying and repairing deformities may include visual and/or machine inspection of the vehicle. Specific lighting conditions may assist in the inspection. For example, a repairer may inspect a panel of a motor vehicle. The inspection may include directing a light source toward the exterior surface of the motor vehicle. The inspection may include observing a panel of a motor vehicle at a plane substantially perpendicular to the exterior surface of the motor vehicle while the light illuminates the panel. In some examples the light source may be positioned such that the light emitted from directly from the light source illuminates the exterior surface of the panel of the motor vehicle. In some examples, the light source may be position substantially perpendicular to the exterior surface of the panel of the motor vehicle to emit light onto the exterior surface of the motor vehicle directly from the light source.

The repairer may identify the position, extent, and/or topography of a deformity on the exterior surface of a panel of the motor vehicle by observing the motor vehicle panel under illumination by the light source. For example, the repairer may be able to observe the deformity in the motor vehicle repair panel in the reflection of the light source off the exterior surface on the panel of the motor vehicle. For example, an incident ray of light may exit the light source, such as a fluorescent bulb or light emitting diode (LED), and strike the exterior surface of the motor vehicle. A reflected ray of light may be reflected off the exterior surface of the motor vehicle and be observable by the repairer. As a result, the repairer may observe a reflection of an image of the light source.

However, when the panel of a motor vehicle includes a exterior surface deformity, the angles of the deformed portion of the exterior surface of the motor vehicle panel may be inclined at different angles relative to the non-deformed portion of the exterior surface of the motor vehicle panel. Consequently, a portion of the incident rays exiting the light source may strike the differently inclined angles and the reflected rays may be reflected off the deformed exterior surface at different angles than the reflected rays that are reflected off the non-deformed exterior surface. As a result, the visible reflection of the image of the light source may appear diffuse, distorted, and/or have an altered luster at the deformed portions of the exterior surface of the vehicle panel. As the repairer performs the repair of the deformity, the repairer may monitor the reflection during the process in order to restore the topography of the exterior surface of the vehicle such that the reflection appears substantially uniform.

As described above, light sources for identifying and repairing deformities to the exterior surface of motor vehicles may shine light directly from the source onto the exterior surface of the vehicle panel. The light emitted directly from florescent bulbs or LED light sources off the exterior surface of the vehicle panel into the eye of a repairer may be relatively bright and/or of a relatively high intensity. Such light may strain and/or fatigue the eyes of the repairer. Prolonged exposure to such light may result in aches, pains, injuries, missing a deformity present on an exterior surface of a vehicle panel, misidentifying a topology of a deformity present on an exterior surface of a vehicle panel, incorrectly repairing a deformity on an exterior surface of the repair vehicle, and even inadvertently damaging or exacerbating the damage to the exterior surface of the vehicle panel.

Some vehicle lighting apparatuses may include a diffuser between the light source and the vehicle panel. That is some vehicle lighting apparatuses may include a diffuser over the light source such that the light may be emitted directly from the light source through the diffuser onto the vehicle panel. However, the diffusers may be inadequate to reduce the brightness and/or intensity of the light source to a level that does not have negatively affect the repairer and/or the repairer's ability to perform repairs for prolonged periods of time.

In some examples, having a striped appearance to the light sources in the vehicle lighting apparatus may assist in the identification of the position, extent, and/or topography of a deformity on the exterior surface of a vehicle panel. For example, the appearance of a plurality of light and dark portions emitted from a light source may create variable lighting conditions that help to light the deformities in different ways leading to a quicker and/or more accurate identification of the deformities on the exterior surface of the vehicle panel. Some examples of vehicle lighting apparatuses may include a plurality of light sources such as bulbs and/or a plurality of LED strips that are arranged to produce the stripes as areas of bright and intense lighting where the light sources are located and areas of relatively less bright and relatively less intense lighting where the light sources are not located. The use of the plurality of light sources arranged in stripes may exacerbate the negative effects of the bright and/or intense light by adding more light sources from which light directly exits and is directly reflected from the vehicle panel to the eyes of the repairer. Additionally, the use of the plurality of light sources introduces an increased possibility for electrical failure or light source damage with the increased amount of light sources.

Further, the vehicle lighting apparatuses with a plurality of light sources arranged in stripes may utilize substantially more power than a vehicle lighting apparatus with a fewer light sources. Beyond the conservation and cost-of-operating concerns associated with the increased power consumption by a plurality of light sources, such vehicle lighting apparatuses may have limited utility in performing the repairs. For example, repairing a deformity may occur in a facility such as a body shop. In such facilities, power outlets may be plentiful, but the utilization of long power cords and/or adapters to provide power to such a vehicle lighting apparatus may make the vehicle apparatus unwieldy to move around, creating a tripping hazard while working around the vehicle, and/or introduce a potential damage point or failure point for the apparatus. It may be desirable to have a light-weight and maneuverable vehicle lighting apparatus for quickly adjusting, manipulating, and maneuvering around the vehicle while repairing deformities. As such, a vehicle lighting apparatus that utilizes a battery power source may lend itself to such light-weight maneuverability. However, battery supplies may have a fixed supply of power that can be used before the battery supply is recharged or replaced. Consequently, a vehicle lighting apparatus with a plurality of light sources may consume the power supply of the battery more rapidly than one with fewer light sources and, as a result, may have a reduced operational capacity or run time before a battery recharge or replacement is needed to restore function.

In some examples, repairing a deformity may occur outside or in a facility without available power outlets. For example, a deformity repair business may include a mobile paintless dent removal business that travels to the location of the vehicle to perform a vehicle deformity removal service. In such examples, the equipment, including the vehicle lighting apparatus may need to utilize a battery power supply to power the light source. In such examples, the amount of battery power consumed by the vehicle lighting apparatus may limit the amount of time the service may be performed, the ability to utilize other battery powered equipment from the battery supply, and the ability to meet repair deadlines.

In contrast, examples of the present disclosure may include a vehicle lighting apparatus that is lightweight, maneuverable, and may provide a softer light while retaining the option for a striped appearance, all with an option for relatively reduced power requirements. For example, examples of the present disclosure may include a vehicle lighting apparatus, comprising: a backing panel; a light guide panel (LGP) layered over the backing panel, wherein the LGP includes a front surface, a rear surface opposite the front surface, and a plurality of side surfaces connecting the front surface with the rear surface; a light source positioned along a first side surface of the plurality of side surfaces of the LGP; and a front film layered over the front surface of the LGP, wherein the LGP includes a plurality of refraction elements that refract light emitted from the light source through the front surface of the LGP and through the front film and wherein a distribution pattern of the refraction elements creates a corresponding pattern of differing light intensities visible through the front film when illuminated by the light source.

Figure 1:
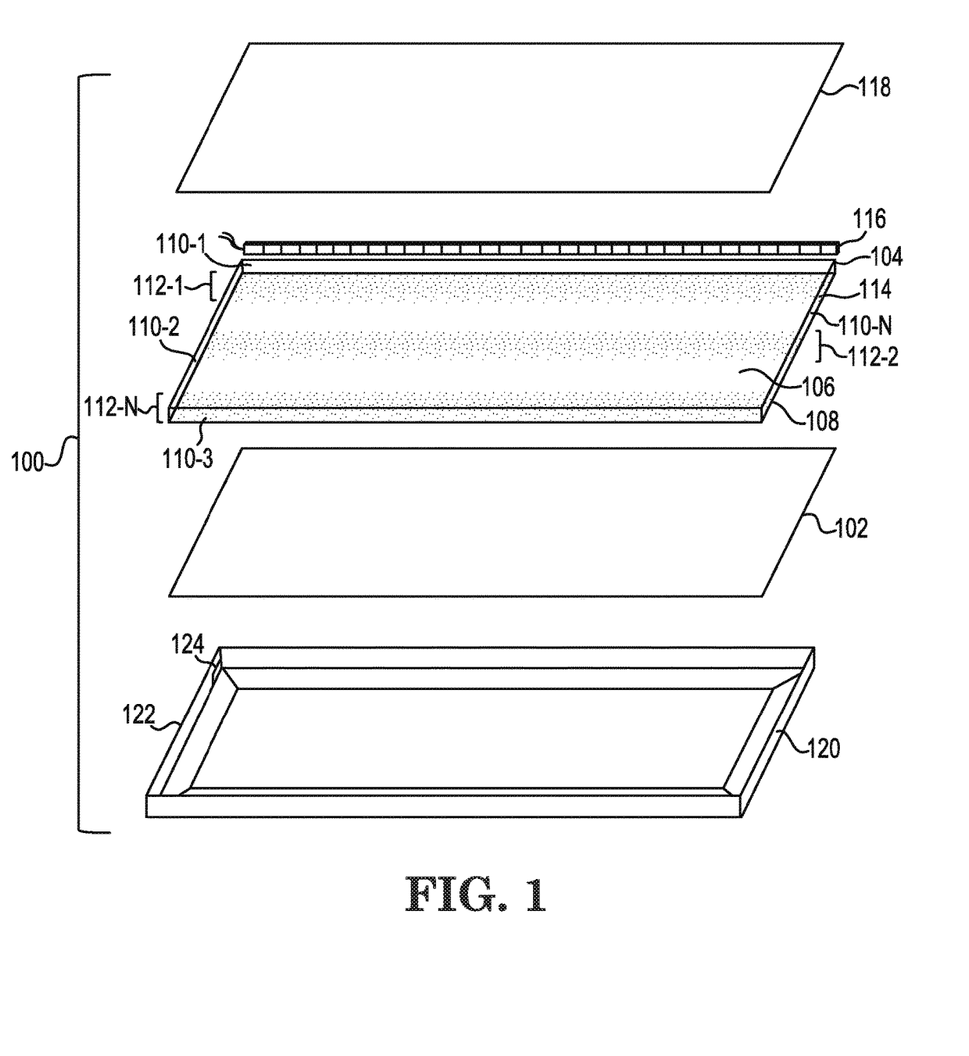
FIG. 1 illustrates an example of a disassembled vehicle lighting apparatus consistent with the disclosure.

FIG. 1 illustrates a disassembled vehicle lighting apparatus 100 consistent with the disclosure. The vehicle lighting apparatus 100 may include a backing panel 102. A backing panel 102 may include a sheet of material that is approximately the same dimensions as or slightly larger a light guide panel (LGP) 104. The backing panel 102 may be lightweight and flexible. The backing panel 102 may be constructed from a material that restricts the amount of light that passes through the backing panel 102. For example, the backing panel 102 may be constructed of a substantially opaque material. For example, a backing panel 102 may be a light weight and substantially opaque film.

The backing panel 102 may be reflective. For example, the backing panel 102 may be a substantially opaque film with a reflective coating. For example, the backing panel may include a glossy finish on its surface that reflects light from its surface. The backing panel 102 may have a substantially smooth and/or regular surface to reflect light off of.

The vehicle lighting apparatus 100 may include an LGP 104. The LGP 104 may include a substantially transparent panel. The LGP 104 may be constructed of a transparent acrylic panel. For example, the LGP 104 may be constructed of a poly(methyl methacrylate), also known as acrylic or acrylic glass, shatter-resistant transparent thermoplastic. The LGP 104 may allow light to pass through the body of the LGP 104.

The LGP 104 may include a front surface 106. The front surface 106 may be substantially flat and/or smooth. That is, the front surface 106 may be non-textured. The front surface 106 may appear transparent, however items in the body of the LGP 104 and/or on the other surfaces of the LGP 104 may be visible through the transparent front surface 106. The front surface 106 may allow light to escape from the body of the LGP out through the front surface.

Additionally, the LGP 104 may include a rear surface 108. The rear surface 108 of the LGP 104 may be a surface of the LGP 108 that is opposite the front surface 106. The rear surface 108 may be a surface of the LGP 104 that is parallel to the first surface 106. The rear surface 108 of the LGP 104 may have the same dimensions as the first surface 106. The rear surface 108 of the LGP 104 may allow light to escape from the body of the LGP 104 out through the rear surface 108 and may also allow light to renter the body of the LGP 104 through the rear surface 108.

The LGP 104 may include a plurality of side surfaces 110-1 . . . 110-N. The plurality of side surfaces 110-1 . . . 110-N may be surfaces 110-1 . . . 110-N of the LGP 104 that connect the front surface 106 to the rear surface 108. The side surfaces 110-1 . . . 110-N may be substantially perpendicular to the front surface 106 and the rear surface 108. The side surfaces 110-1 . . . 110-N may be substantially smooth or non-textured. In some examples, one or more of the side surfaces 110-1 . . . 110-N may bare tooling marks or imperfections that have clouded the one or more of the side surfaces 110-1 . . . 110-N. In some examples, one or more of the side surfaces 110-1 . . . 110-N may be polished to remove any clouding from the surface and restore transparency to allow light to transmit freely through the surface. In some examples, one or more of the side surfaces 110-1 . . . 110-N may include an added reflector or reflective coating covering the one or more side surfaces 110-1 . . . 110-N along their respective lengths in order to reflect light back into the body of the LGP 104 instead of allowing it to escape the side surfaces 110-1 . . . 110-N of the LGP 104.

A first side surface 110-1 of the plurality of side surfaces 110-1 . . . 110-N may be one of the one or more of the plurality of side surfaces 110-1 . . . 110-N that is transparent and/or does not include a reflector or reflective coating on the surface. The first side surface 110-1 of the plurality of side surfaces 110-1 . . . 110-N may be one of the one or more of the plurality of side surfaces 110-1 . . . 110-N that may allow light to enter into the body of the LGP 104 there through.

The vehicle lighting apparatus 100 may include a light source 116. The light source 116 may include an LED. In some examples, the light source 116 may include a strip of LEDs. The strip of LEDs may include a flexible circuit board populated along its length on one surface with LEDs. The light source 116 may be positioned along the first side surface 110-1 of the LGP 104. The light source 116 may be positioned along substantially an entire length of the first side surface 110-1 of the LGP 104. The light source 116 may be positioned along the first side surface such that it emits light directly from the light source into the body of the LGP 104 through the first side surface 110-1. The light source 116 may be substantially the same height and width as the first side surface 110-1, such that the light emitted by the light source 116 travels directly into the body of the LGP 104 and is not transmitted beyond the dimensions of the first side surface 110-1. Transmitting light beyond the dimensions of the first side surface 110-1 may result in undesirable direct lighting on and/or across the first surface 106 of the LGP 104 and/or the second surface 108 of the LGP 104 without passing through the body of the LGP 104. In the above described examples of the strip of LEDs, the LEDs may be positioned between the flexible circuit board and the first side surface 110-1 of the LGP 104. There may not be LEDs on the side of the flexible circuit board that is opposite the side including the LEDs that is interfaced against the first side surface 110-1 of the LGP 104. The light source 116 may include a reflector positioned behind the light source relative to the first side surface 110-1 of the LGP 104. The reflector may reflect light from the LED that is not directly entering the body of the LGP 104 and/or any light that was reflected off the first side surface 110-1 of the LGP 104 back into the body of the LGP 104 through the first side surface 110-1. In examples including LED strips, the surface of the side of the flexible circuit board with LEDs may be reflective.

The light source 116 may include connections, such as wires or male/female adapters, that lead from the vehicle lighting apparatus 100 to a power source. For example, the light source 116 may include a connection to a wall outlet and/or a mobile battery power source. The light source 116 may include connections that lead from the vehicle lighting apparatus 100 to other vehicle lighting apparatuses such that a plurality of vehicle lighting apparatuses may be operated together and/or form a single power supply.

The LGP 104 may include a plurality of refraction elements such as refraction element 114. A refraction element 114 may include a modification to the rear surface 108 of the LGP 104. For example, the modification may include a pattern, such as a grid, a triangle, a vertical line, a horizontal line, a vertical v-groove a dot, a groove, etc. that is introduced to the rear surface 108 and/or the body of the LGP 104. The refraction element 114 may be introduced by cutting, heating, laser marking, or otherwise marring the rear surface 108 of the LGP 104. The refraction element 114 may be introduced by printing the patterns onto the LGP 104 using light-scattering diffusive ink. The refraction element 114 may include light-scattering particulates that are added to the resin of the LGP 104 as it is being formed so that the light-scattering particulates are embedded within the body of the LGP 104.

A refraction element 114 may refract light resulting in the redirection of the light along a new path. For example, a refraction element 114 may refract light emitted from the light source 116 through the front surface 106 of the LGP 104. For example, light may be emitted from the light source 116 and travel through the first side surface 110-1 of the LGP 104 and into the body of the LGP 104. The light may travel through the LGP 104 along a plane extending from the light source 116 through the first side surface 110-1 and to the third side surface 110-3. The light may encounter a refraction element 114, such as a laser etched dot depression protruding into the body of the LGP 104 from the bottom surface 108 of the LGP 104. When the light encounters a refraction element 114 the refraction element may refract the light traveling along the plane extending from the light source 116 through the first side surface 110-1 and to the third side surface 110-3 to a second plane. In some examples, the refraction element 114 may refract the element directly from the plane extending through the body of the LGP 104 from the light source 116 through the first side surface 110-1 and to the third side surface 110-3 to a second plane that transmits the light out the front surface 106 of the LGP through the area of the front surface 106 directly above the refraction element 114.

In another example, the light may encounter a refraction element 114 and the refraction element 114 may refract the light traveling along the plane extending from the light source 116 through the first side surface 110-1 and to the third side surface 110-3 to a second plane that transmits the light out of the rear surface 108 of the LGP 104 through the area of the rear surface 108 where the refraction element 114 is located. As described above, the light refracted out the rear surface 108 of the LGP 104 may encounter the backing panel 102 and be reflected back into the LGP 104. For example, the light refracted out the rear surface 108 of the LGP 104 by a refraction element 114 may be reflected back at the rear surface 108, and may travel through the refraction element 114 and/or the area of the rear surface 108 immediately around the refraction element and out through the front surface 106 of the LGP through the area of the front surface 106 directly above the refraction element 114. Additionally, light that may incidentally escape the rear surface 108 of the LGP 104 may also be reflected by the backing panel 102 into the rear surface 108 and may travel through the refraction element 114 and/or the area of the rear surface 108 immediately around the refraction element and out through the front surface 106 of the LGP 104 through the area of the front surface 106 directly above the refraction element 114.

As a result of the lighting arrangement described above, the LGP 104 may have a very softy light, low intensity, and glowing appearance when lit. The refraction elements 114 may create areas of increased light emissions and/or intensity of light emitted through the portions of the front surface 106 of the LGP 104 directly above the refraction elements 114 relative to the portions of the front surface 106 of the LGP 104 that are not located above the refraction element 114. That is, the area of the LGP 104 above the refraction elements 114 may appear to be lit brighter or to a higher light-intensity than the remainder of the LGP 104. In some examples, the portions of the LGP 104 that are not above refraction elements 114 may appear darker or lit to a lower light intensity that the areas above the refraction elements 114. For example, the portions of the LGP 104 that are not above refraction elements 114 may appear substantially unlit or lit to a dim background glow compared to the portions above the refraction elements 114. The effect may result from the areas of the LGP 104 that are not above the refraction elements 114 being illuminated by incidental glow of the light traveling through the body of the LGP along the plane extending from the light source 116 through the first side surface 110-1 and to the third side surface 110-3, while the areas of the LGP 104 that are located above the refraction elements 114 are the areas where the light is being refracted and/or reflected out of the body of the LGP 104 through the front surface 106 and into the environment to illuminate the exterior surface of the vehicle.

In some examples, the LGP 104 may include a plurality of refraction elements 114 distributed in patterns across the bottom surface 108 of the LGP 104. For example, the plurality of refraction elements 114 may be distributed into stripes 112-1 ... 112-N of refraction elements 114. It should be understood that stripes 112-1 ... 112-N are not the only type of distribution pattern for refraction elements 144 that may be utilized on the LGP 104 and other examples of patterns and/or pattern orientations apply equally to this disclosure. The refraction elements 114 may be distributed as distinct and/or separate stripes 112-1 ... 112-N of refraction elements 114 running across the LGP 104 from one side surface to an opposing side surface 110-1 ... 110-N. The stripes 112-1 ... 112-N of refraction elements 114 may be separated from one another by intervening portions of the LGP that do not include refraction elements 114.

As described above, the distribution of refraction elements 114 may affect the distribution of the light emitted from the vehicle lighting apparatus 100. In examples where the refraction elements 114 are distributed in patterns, such as the stripes 112-1 ... 112-N, the light emission from the vehicle lighting apparatus 100 may have a same pattern. That is, the vehicle lighting apparatus 100 may include a distribution pattern of the refraction elements 114 that creates a corresponding pattern of differing light intensities visible through the front surface 106 of the LGP 104 when illuminated by the light source 116.

For example, the LGP 104 may include two portions: a first portion with the refractions elements 114 and a second portion without the refraction elements 114. The first portion and the second portion may form the alternating stripes 112-1 ... 112-N of refractions elements 114 across the rear surface 108 of the LGP 104 that faces the backing panel 102. The distribution pattern of the alternating stripes 112-1 ... 112-N may create a corresponding pattern of differing light intensities visible through the front surface 106 of the LGP 104 when illuminated by the light source. For example, the corresponding pattern of differing light intensities may include alternating stripes of a greater light intensity, corresponding to the first portion, and stripes of a lesser light intensity, corresponding to the second portion. As such, the vehicle lighting apparatus 100 may illuminate the exterior surface of the vehicle with alternating light stripes (e.g., relatively higher light intensity and/or brightness) and dark stripes (e.g., relatively lower light intensity and/or brightness) emitted from the corresponding portions of the LGP 104. As described above, the alternating patterns of differing light intensities may make identification of deformities on the exterior surface of the vehicle easier and/or more accurate.

The vehicle lighting apparatus 100 may provide the alternating patterns of differing light intensities without the use of a plurality of light sources. This may provide an energy savings. However, the vehicle lighting apparatus 100 may include more than one light source 116. Since the vehicle lighting apparatus 100 utilizes edge-lighting and emits light from the light source 116 into the body of the LGP 104 through a side surface 110-1 ... 110-N, the vehicle lighting apparatus 100 may include lighting sources 116 along any of and/or each of the side surfaces 110-1 ... 110-N. Unlike the vehicle lighting apparatuses that utilize the plurality of light sources to delineate patterns, the plurality of light sources in the vehicle lighting apparatus 100 according to the present disclosure may be utilized to add or subtract light intensity from the lighting patterns generated by the refraction elements 114. As such, the vehicle lighting apparatus may include an adjustable light level that may adjust the brightness of light delivered by a single lighting source 116 and/or by each of a plurality of lighting sources. In some examples, the plurality of lighting sources may include distinct types of lighting sources. For example, a first lighting source of a plurality of lighting sources may have a first color temperature bulb and/or LED, such as a soft white 2700K-3000K, and a second lighting source of the plurality of lighting sources may have a second color temperature bulb and/or LED, such as bright white (3500K-4100K). In such examples, the color temperature and/or mix of color temperature of light emitted by the vehicle lighting apparatus 100 may be adjustable.

Further, unlike a vehicle lighting apparatus that utilizes the light from a plurality of light source shined directly from the light source at the vehicle, the vehicle lighting apparatus 100 of the present disclosure may utilize indirect lighting from a single light source 116 to illuminate the exterior surface of the vehicle. That is, the light may exit the light source 116, transmit through a side surface of the LGP 104, enter the body of the LGP 104, and be selectively refracted and/or reflected from the body of the LGP 104 out specific portions of the front surface 106 of the LGP 104. The result may be emission of a light from the vehicle lighting apparatus 100 that is more diffuse, less intense, less bright, less concentrated, and/or less harsh to the repairer's eyes. The light emitted from the vehicle lighting apparatus 100 may be further softened by transmitting the light exiting the front surface 106 of the LGP 104 through a font film 118 layered over the front surface 106 of the LGP 106. The front film 118 may be translucent film. In some examples, the front film 118 may be a light diffusing panel constructed from a plastic material. In some examples, the front film 118 may be a colored panel that alters the hue of the light transmitted from the front surface of the LGP 104 through the front film 118. In some examples, the front film 118 may include a pattern printed on the front film 118. The pattern on the front film 118 may block a portion of the light transmitted from the front surface of the LGP 104 through the front film 118. In some examples, the pattern on the front film 118 may include a pattern of alternating light and dark stripes, where the light stripes include unprinted portions of the front film 118 and the dark striped include the light blocking printed portions of the front film 119.

The vehicle lighting apparatus 100 may include a frame 120. The frame 120 may include a tray-like frame that the other components of the vehicle lighting apparatus 100 can be nested within. For example, the backing panel 102 may be fit within and to the bottom of the frame 120, the light source the LGP 104 may be fit within the frame 120 and on top of the backing panel 102, and the front film 118 may be fit within the frame 120 and on top of the LGP 104. The above described components may be sandwiched within the frame 120 such that the front surface of the LGP 104 and/or the front film 118 is substantially level with the top lip 122 of the frame 120. The frame 120 may also include an aperture 124 that provides passage for the electrical connectors of light source 116 to pass through the frame 120 in order to reach a power supply.

The frame 120 may be constructed of a lightweight metal material. The frame 120 may include reflective surfaces. In some examples, the inner portion of the frame 120 may act as a reflector. Since the inner portion of the frame 120 will be positioned against the side surfaces 110-1 ... 110-N of the LGP 104, the inner portion of the frame 120 may reflect light escaping the body of the LGP 104 back into the body of the LGP 104.

Figure 2:
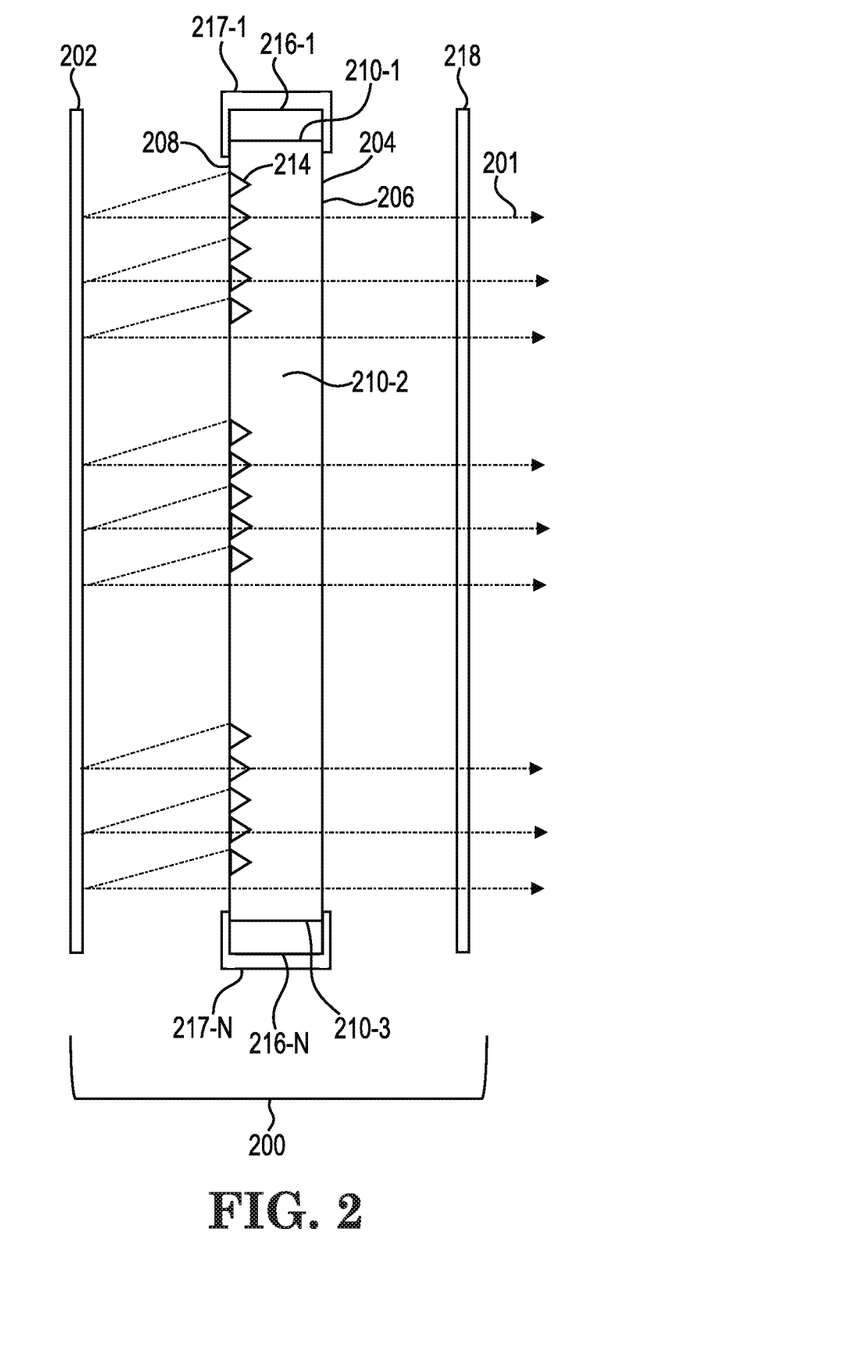
FIG. 2 illustrates an example of a side profile view of a disassembled vehicle lighting apparatus according to the present disclosure.

FIG. 2 illustrates a side profile view of a disassembled vehicle lighting apparatus 200 according to the present disclosure. The vehicle lighting apparatus 200 may include a reflective backing panel 202. The vehicle lighting apparatus 200 may include an LGP 204. The LGP 204 may include a plurality of refraction elements 214. The refraction elements 214 may include a laser etched depression in the rear surface 208 of the LGP 204 that is facing the backing panel 202.

The vehicle lighting apparatus 200 may include a light source 216-1. In some examples the vehicle lighting apparatus 200 may include a plurality of light sources 216-1 . . . 216-N. A first light source 216-1 may be positioned against a first side surface 210-1 of the LGP 204. The first light source 216-1 may emit light directly into the body of the LGP 204 through the first side surface 210-1. A second light source 216-N may be positioned against a second side surface 210-3 of the LGP 204. The second light source 216-N may emit light directly into the body of the LGP 204 through the second side surface 210-3.

The vehicle lighting apparatus 200 may include a plurality of reflectors 217-1 . . . 217-N. The reflectors 217-1 . . . 217-N may reflect light from the corresponding light source 216-1 . . . 216-N and/or light escaping out of the corresponding side surface 210-1 . . . 210-N back into the body of the LGP 204 through the corresponding side surface 210-1 . . . 210-N. The reflector 217-1 . . . 217-N may include a reflective coating. In other examples, the reflector 217-1 . . . 217-N may be a portion of the frame 120 described with respect to FIG. 1. In such examples, the reflector 217-1 . . . 217-N may be wide enough to accommodate a sandwich of the backing panel 202, the LGP 204 and/or light source 216-1 . . . 216-N, and the front film 218.

The illustration of the vehicle lighting apparatus 200 in FIG. 2 includes an illustration of light paths, such as light path 201, illustrated as dashed lines. In an example, the light path 201 may be a light path of light that that is emitted from the light source 216-1. The light may enter the body of the LGP 204 through the first side surface 210-1 of the LGP 204. The light may travel along a first path from the light source 216-1 through the body of the LGP 204 in a plane substantially parallel to the front surface 206 and the rear surface 208 of the LGP 204. However, the light may encounter a refraction element 214. The light may be refracted from the first path to the light path 201. The light may be refracted, at the refraction element 214, out of the rear surface 208 of the LGP 204, where it may proceed until it encounters the backing panel 202. The reflective backing panel 202 may reflect the light on light path 201 back into the body of the LGP 204 through the rear surface 208 of the LGP 204. The reflected light may travel out the front surface 206 of the LGP 204 along the light path 201 in a plane that is substantially perpendicular to the front surface 206 and the rear surface 208 of the LGP 204. As such, the light may pass through the front film 218 along the same path. As a result, the portions of the front surface 206 of the LGP 204 that are located immediately above the refraction elements 214 will be the portions that appear to be emitting the greatest amount of light and/or the brightest light. The portions of the front surface 206 of the LGP 204 that are not located immediately above the refraction elements 214 will be the portions that appear to be dim and not emitting light.

Figure 3:
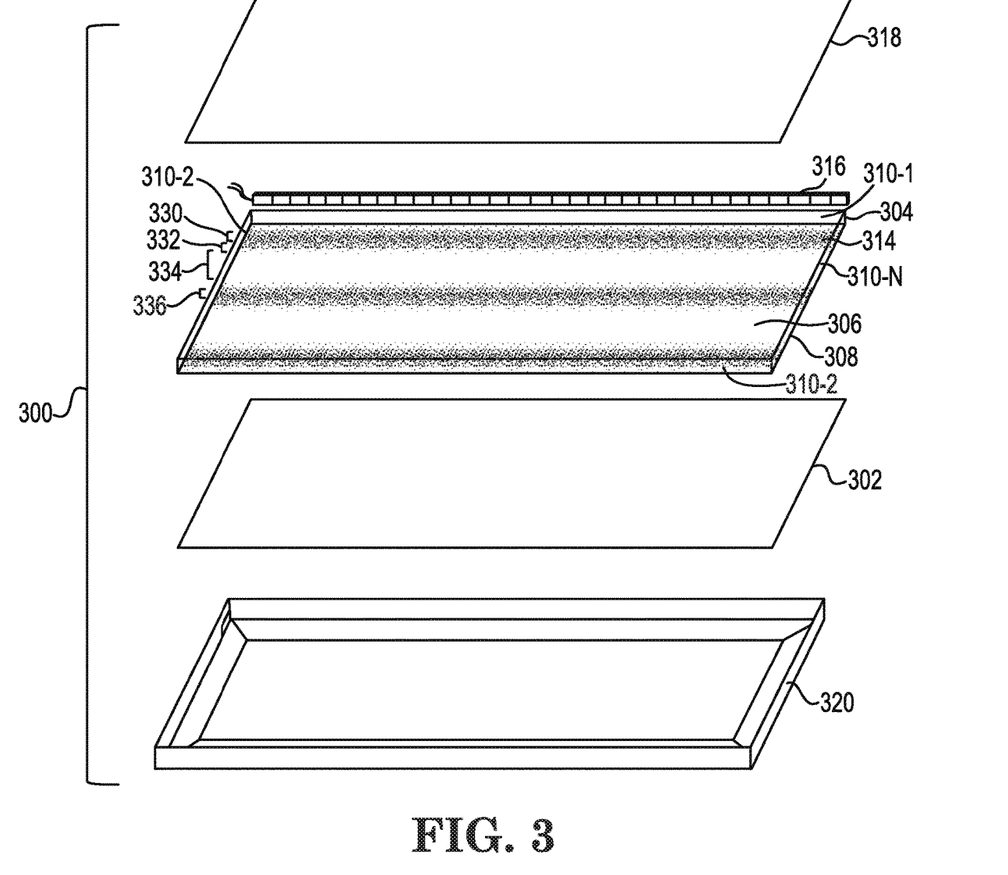
FIG. 3 illustrates an example of a disassembled vehicle lighting apparatus consistent with the disclosure.

FIG. 3 illustrates a disassembled vehicle lighting apparatus 300 consistent with the disclosure. The vehicle lighting apparatus may include a LGP 304. The LGP 304 may include a front surface 306. The LGP 304 may include a rear surface 308 that is opposite and parallel to the front surface 306. The LGP 304 may include a plurality of side surfaces 310-1 . . . 310-N. The plurality of side surfaces 310-1 . . . 310-N may connect the front surface 306 with the rear surface 308. A face of the first side surface 310-1 of the LGP 304 and a face of the front surface 306 of the LGP 304 may be perpendicular to each other. The LGP 304 may be a transparent from the front surface 306 to the rear surface 308. The side surfaces 310-1 . . . 310-N, other than the side surface where a light source 316 is positioned against, may include a reflective coating and or a reflective backing to reflect light escaping the body of the LGP 304 through the side surfaces 310-1 . . . 310-N back into the body of the LGP 304 through the side surfaces 310-1 . . . 310-N. In some examples, the reflector may include a side surface reflector positioned against a face of a side surface 310-1 . . . 310-N. For example, the reflector may include a portion of the frame 320 acts as a side surface reflector positioned against a face of a side surface 310-1 . . . 310-N.

The vehicle lighting apparatus 300 may include a light source 316. The light source 316 may include a powered LED light source. The LED light source may be powered from a battery power source, a wall outlet power source. The LED light source may be connected to a powered LED light source of another vehicle lighting apparatus and the LED light source may draw its power from and/or through the another vehicle lighting apparatus.

The light source 316 may be positioned along a first side surface 310-1 of the LGP 304 such that the light produced by the light source 316 enters the LGP 304 through the first side surface 310-1. The light source 316 may include and/or be encased in a reflector that may reflect light from the light source 316 into the body of the LGP 304 through the first side surface 310-1. As with other examples, additional light sources may be positioned along other side surfaces 310-1 . . . 310-N of the LGP 304.

The vehicle lighting apparatus 300 may include a backing panel 302. The backing panel 302 may be a reflector panel. The backing panel 302 may be positioned against the rear surface 308 of the LGP 304 such that a portion of the light produced by the light source 316 that exits the rear surface 308 of the LGP 304 (e.g., as incidental light leakage and/or as light refracted by a refraction element 314) is reflected back into the body of the LGP 304 through the rear surface 308 of the LGP 304 by the backing panel 302.

The LGP 304 may include a plurality or refraction elements, such as refraction element 314. A refraction element 314 may include a depression introduced in the rear surface 308 of the LGP 304 that protrudes into the body of the LGP 304. The refraction element 314 may have the appearance of a dot on the rear surface 308 of the LGP 304. The geometry of the refraction element 314 may include a geometry configured to refract light that encounters the refraction element 314 as is it emitted through the body of the LGP 304 such that the light is refracted out the rear surface 308 onto the backing panel 302 where it is reflected back to the rear surface 308 and out the front surface 306 of the LGP 304 at the refraction element 314. Additionally, the geometry of the refraction element 314 may include a geometry configured to refract light that encounters the refraction element 314 as is it emitted through the body of the LGP 304 such that the light is refracted out the front surface 306 of the LGP 304 at the refraction element 314. In some examples, the refraction element 314 may be a dot laser etched into the rear surface 308 of the LGP 304.

The plurality of refraction elements may be distributed in a distribution pattern across the LGP 304. Each refraction element 314 may create a brighter light emission out of the portion of the front surface 306 located above the refraction element 314. Since the plurality of refraction elements refract the light produced by the LED light source to exit the front surface of the LGP 304, the distribution pattern of the plurality of refraction elements may create a corresponding pattern of differing light intensities visible through the front film 318 when illuminated by the light source 316. For example, the plurality of refraction elements may be distributed at a first density across a first portion 330 of the LGP 304 and a second portion 336 of the LGP 304. A density may refer to the amount of refraction elements per unit of surface area of the LGP 304, an amount of a surface area of the LGP 304 occupied by refraction elements, and/or a size of refraction elements in a surface area of the LGP 304. The first portion 330 and the second portion 336 of the LGP 304 may include horizontal parallel stripes traversing the LGP 304 from one side surface 310-2 to another side surface 310-N. The first density may be a relatively greatest density of refractive elements and/or a relatively densest refractive element distribution. The first density may include the largest amount of refractive elements per surface area of the LGP 304, the largest amount of surface area of the LGP 304 covered by refraction elements, and/or the largest size of refraction elements relative to the other portions of the LGP 304. The first portion 330 may create a corresponding brightest area and/or an area of highest light intensity visible through the front surface 306 of the LGP 304 above the first portion 330 and the second portion 336 of refraction elements.

The plurality of elements may be distributed at a second density across a third portion 334 of the LGP 304. The third portion 334 may include a horizontal stripe that is traversing the LGP 304 parallel to the first portion 330 and the second portion 336 from one side surface 310-2 to another side surface 310-N. The third portion 334 may separate the first portion 330 and the second portion 336 of the LGP 304. The second density may be a relatively lowest density of refractive elements and/or a relatively least dense refractive element distribution. The second density may include the smallest amount of refractive elements per surface area of the LGP 304, the smallest amount of surface area of the LGP 304 covered by refraction elements, and/or the smallest size of refraction elements relative to the other portions of the LGP 304. In some examples, the second density may include no refraction elements and, as such, the third portion 334 may include no refraction elements. The third portion 334 may create a corresponding dimmest area and/or an area of lowest light intensity visible through the front surface 306 of the LGP 304 above the third portion 334.

Additionally, the plurality of refraction elements may be distributed at a third density across a fourth portion 332 of the LGP 304. The fourth portion 332 may include a horizontal stripe that is traversing the LGP 304 parallel to the first portion 330, second portion 336, and the third portion 334 from one side surface 310-2 to another side surface 310-N. The fourth portion 332 may separate the first portion 330 from the third portion 334. The third density may be a density that is greater than the second density of refraction elements, but less than the first density. The third density may include the amount of refractive elements per surface area of the LGP 304 that is greater than the second density but less than the first density, the amount of surface area of the LGP 304 covered by refraction elements that is greater than the second density but less than the first density, and/or the size of refraction elements relative to the other portions of the LGP 304 that is greater than the second density but less than the first density. The fourth portion 332 may create a corresponding area of a brightness or light intensity visible through the front surface 306 of the LGP 304 above the fourth portion 332 that is greater than the one corresponding to the third portion 334, but less than the one corresponding to the first portion 330 and the second portion 336.

For example, the plurality of refraction elements may be distributed in a density gradient. The center of a stripe of the plurality of refraction elements may be the densest distribution of refraction elements and the density of the refraction elements may dissipate further from the center of the stripe vertically in both directions until they reach a portion where no refraction elements are located. For example, a density gradient from a greater density of refraction elements to a lesser density of refraction elements may be formed from the first portion 330 of the LGP 304, across the fourth portion 332, and ending in no refraction elements in the third portion 332. The LGP 304 may include a plurality of stripes of refraction elements traversing the bottom surface 308 of the LGP 304 from side surface (e.g., 310-2) to side surface (e.g., 310-N). Each of the stripes may include the density gradient of the refraction elements described above.

The plurality of refraction elements may be distributed to project a plurality of stripes through the face of the font film 318 light diffusing panel when the light source 316 is emitting the light. As a result of the density gradient distribution of the plurality of refraction elements within the stripe patterns, the stripes may emit a corresponding illumination gradient. The portions of the stripe that have the highest density of refraction elements may create a brightest and/or most intense illumination at the area of the LGP 304 above the highest density of refraction elements. The brightness and/or illumination intensity may appear to dim proportional to the gradually lower density refraction elements in less densely distributed portions of the stripe proportion. In some examples, a first portion of the plurality of stripes corresponding to, for example, the first portion 330 of the LGP 304 may have an illuminated appearance. A second portion of the plurality of stripes corresponding to, for example, the fourth portion 332 of the of the LGP 304 may have a darker appearance than the first portion of the plurality of stripes. A third portion of the plurality of stripes corresponding to, for example, the third portion 334 of the LGP 304 may have a darker appearance than the first portion of the plurality of stripes and the second portion of the plurality of stripes.

As described above, the density gradient distribution of the refraction elements may create an illumination gradient of the patterns visible from the LGP 304. The combination of utilizing the illumination patterns along with illumination gradients enhances the repairer's ability to identify the position, extent, and/or topography of a deformity on the exterior surface of a panel of the vehicle when observing the vehicle panel under illumination by the vehicle illumination apparatus 300. For example, the repairer may be able to more accurately observe a deformity in a motor vehicle panel in the reflection of the illumination gradient produced by the vehicle illumination apparatus as the illumination gradient may provide localized variation in the properties and a gradual softening of incident rays of light observed striking the surface of the motor vehicle.

The vehicle lighting apparatus 300 may include a front film 318. The front film 318 may be layered over the front surface 306 of the LGP 304. The front film 318 may include a light diffusing panel. The front film 318 may include a light diffusing panel is a translucent colored panel to alter a hue of the light exiting the front surface 306 of the LGP 304 and passing through the front film 318. The front film 318 may include a printed pattern to block a portion of the light passed through it.

The vehicle lighting apparatus 300 may include a frame 320. The frame 320 may include a tray-like frame that the other components of the vehicle lighting apparatus 300 can be nested within. The frame 320 may include reflective surfaces. In some examples, the inner portion of the frame 320 may act as a reflector. Since the inner portion of the frame 320 will be positioned against the side surfaces 310-1 . . . 310-N of the LGP 304, the inner portion of the frame 320 may reflect light escaping the body of the LGP 304 back into the body of the LGP 304.

Figure 4:
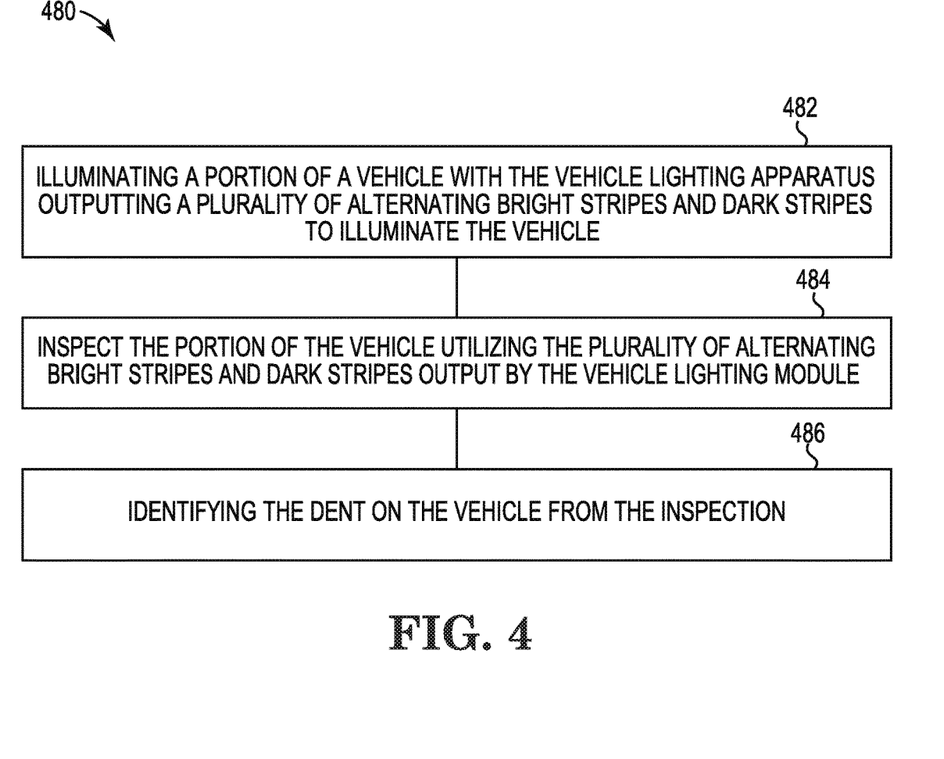
FIG. 4 illustrates a diagram of an example of a method of identifying a dent on a vehicle according to the present disclosure.

FIG. 4 illustrates a diagram of a method 480 of identifying a dent on a vehicle according to the present disclosure. The method 340 is not limited to any particular set and/or order of operations. The method 340 may utilize the vehicle lighting apparatuses described with respect to FIG. 1, FIG. 2, and FIG. 3.

At 482, the method 480 may include illuminating a portion of an exterior surface of a vehicle with a vehicle lighting apparatus. The vehicle lighting apparatus may include a light guide panel (LGP) including a front surface, a rear surface opposite the front surface, and a plurality of side surfaces connecting the front surface with the rear surface. The vehicle lighting apparatus may include a powered light source positioned along a first side surface of the plurality of side surfaces of the LGP such that a light produced by the light source enters the LGP through the first side surface. The vehicle lighting apparatus may include a reflector panel positioned against the rear surface of the LGP such that a portion of the light produced by the light source that exits the rear side of the LGP is reflected back into the LGP by the reflector panel. The vehicle lighting apparatus may include a plurality of refraction elements in the LGP, wherein the plurality of refraction elements refract the light produced by the light source to exit the front surface of the LGP. The plurality of refraction elements may be distributed in alternating stripes of alternating densities across the rear surface of the LGP to produce the output of the plurality of alternating bright stripes and dark stripes when the light source is producing light.

The vehicle lighting apparatus may include a light diffusing panel layered over the front surface of the LGP. The light diffusing panel may include alternating opaque stripes and alternating translucent stripes to produce the output of the plurality of alternating bright stripes and dark stripes. The vehicle lighting apparatus may output a plurality of alternating bright stripes and dark stripes to illuminate the exterior surface of the vehicle. In some examples, the light emitted from the vehicle lighting apparatus may be directed with the plurality of refraction elements that may be distributed in alternating stripes of alternating densities across the rear surface of the LGP to produce the output of the plurality of alternating bright stripes and dark stripes when the light source is emitting light. In some examples, the light diffusing panel may output the plurality of alternating bright stripes and dark stripes by altering the light emitted from the vehicle lighting apparatus with the alternating opaque stripes and alternating translucent stripes to produce the output of the plurality of alternating bright stripes and dark stripes.

Illuminating the vehicle may include positioning the vehicle lighting apparatus so that the light emitted from the front surface of the LGP of the vehicle lighting apparatus is directed at the vehicle. Illuminating the vehicle may include positioning the vehicle illuminating apparatus so that the illumination pattern and/or the illumination gradients thereof are reflected on a panel of the vehicle to be inspected by a repairer. Illuminating the vehicle may include adjusting the lighting intensity and or color temperature of the vehicle illuminating apparatus to provide a clear reflection of the illumination pattern for present lighting conditions and/or vehicle finish properties (e.g., texture, sheen, color, presence of a clear coat, shimmer, etc.). Illuminating the vehicle may include switching out a first front film to a second front film, and/or adding a second front film to the first front film, wherein the second front film may adjust an illumination pattern and/or hue of light emitted by the vehicle lighting apparatus to adjust to present lighting conditions and/or vehicle finish properties.

Illuminating the vehicle may include illuminating the vehicle with a plurality of modular vehicle lighting apparatuses that are combined together. For example, a plurality of modular vehicle lighting apparatuses may be connected together on a stand that directs the vehicle lighting apparatus at the vehicle. A plurality of modular vehicle lighting apparatuses may be electrically connected to one another, such as through adapter connectors, and may draw their power supply from and/or through each other. Utilizing a modular plurality of vehicle lighting apparatuses may allow for scaling up and/or down the amount of illumination of the vehicle to the size of a panel being inspected. As such, the modularity may allow for conservation of power when inspecting small panels or reduced time and effort in inspecting a larger panel by eliminating multiple set ups and/or movements of a smaller vehicle lighting apparatus.

At 484, the method 480 may include inspecting the portion of the vehicle utilizing the plurality of alternating bright stripes and dark stripes output by the vehicle lighting module. Inspecting the portion of the vehicle may include viewing the portion of the vehicle under the illumination of the vehicle lighting apparatus and/or scanning the portion of the vehicle with a sensor to detect surface deformities under illumination by the illumination of the vehicle lighting apparatus. Inspecting the portion of the vehicle may include viewing the portion of the vehicle while the portion of the vehicle is illuminated by the vehicle lighting apparatus and/or the reflection of the vehicle lighting apparatus is visible on the portion of the vehicle.

Inspecting the portion of the vehicle may include the repairer positioning themselves so that they are substantially at eye level with the surface of the vehicle portion being repaired. The repairer may inspect the way the portion of the vehicle reflects the illumination pattern from the vehicle lighting apparatus. The repairer may inspect the portion for areas that do not reflect the illumination pattern from the vehicle lighting apparatus in the same manner as the areas immediately surrounding them.

At 486, the method 480 may include identifying a deformity on the vehicle from the inspection under the illumination by the vehicle lighting apparatus. Identifying the dent may include identify the position, extent, and/or topography of a deformity on the surface of a panel of the motor vehicle by observing the motor vehicle panel under illumination by the light source. Identifying the dent may include prescribing and/or performing a course of repair for the dent.

For example, a repairer may identify a dent on the surface of the portion of the vehicle by identifying reflected rays from the illumination by the vehicle lighting apparatus that are reflected off the dent at a different angle than the reflected rays that are reflected off the non-dented surface. As a result, the visible reflection of the illumination by the vehicle lighting apparatus may appear diffuse, distorted, and/or have an altered luster at the deformed portions of the surface of the vehicle panel. As the repairer performs the repair of the dent, the repairer may monitor the reflection during the process in order to restore the topography of the portion of the surface of the vehicle such that the reflection appears substantially uniform. The repairer may utilize the illumination gradients emitted from the vehicle lighting apparatus to identify the position, extent, and/or topography of a dent on the surface of a panel of the motor vehicle by observing the motor vehicle panel under various portions of the illumination gradients emitted by the light source and highlighting the dent.

The method 480 may be a method of performing paintless dent repair on a motor vehicle by utilizing the vehicle lighting apparatus to identify dents and/or monitor their repair. The paintless dent repair process may include utilizing paintless dent removal tools to push out the dents from the underside of a panel of the vehicle or pulling the panel with glue tabs where the surface paint over the dent is still intact. Since the surface paint over the dent is intact, the dent may be identified based on a different refraction and/or reflection of light from the vehicle lighting apparatus as compared to the area immediately around it. The lightweight, portable, power conserving vehicle lighting apparatus of the present disclosure may provide the alternating patterns with illumination gradients that allow for quick and accurate identification of dents from their distinct reflection or refraction without straining the eyes of the repairer with direct intense lighting conditions. The illumination patterns and gradients provided by the vehicle lighting apparatus may allow for the visual determination of the topography of the dent and determine where the tip of tool being used to push the metal is located behind the vehicle panel. Without the illumination patterns and gradients provided by the vehicle lighting apparatus the fine detail of the dent and/or the repair process may remain unclear to the repairer.

Figure 5:
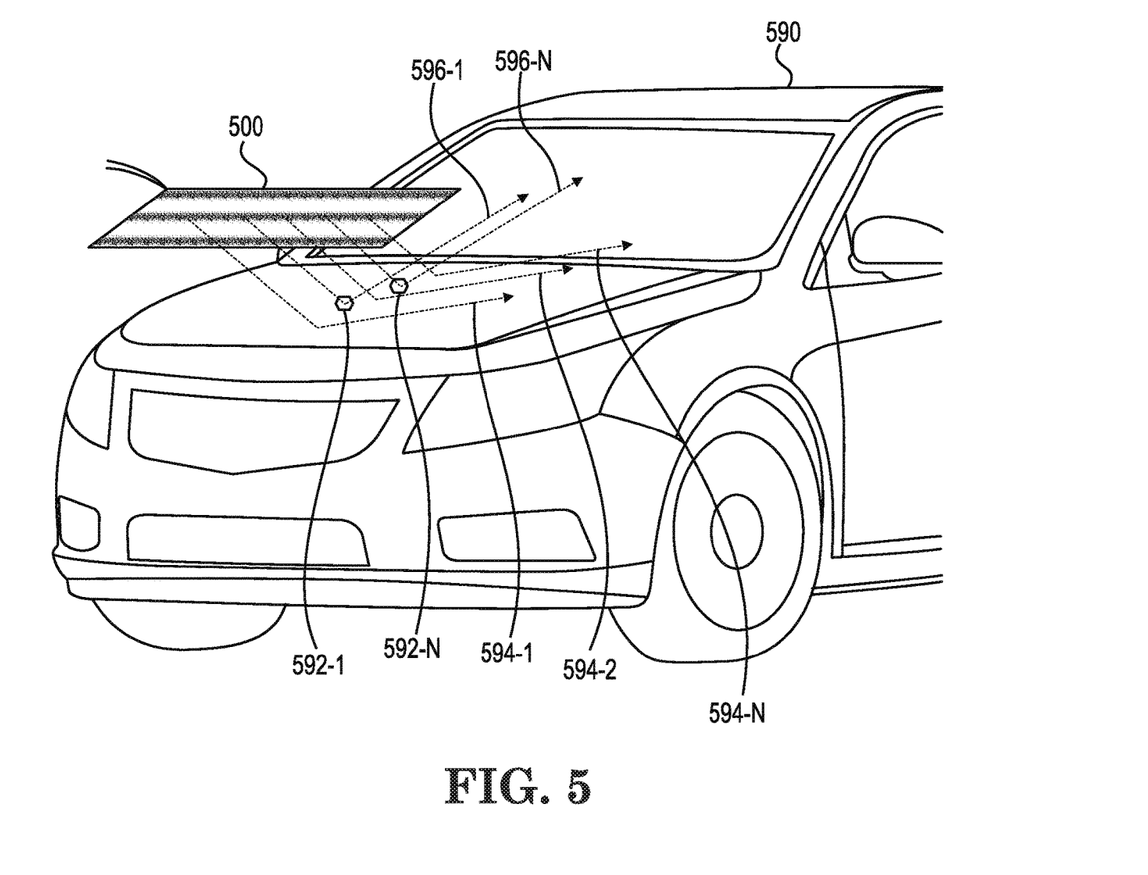
FIG. 5 illustrates a perspective view of an example of a vehicle lighting apparatus utilized to identify a deformity on a vehicle according to the present disclosure.

FIG. 5 illustrates a perspective view of an example of a vehicle lighting apparatus 500 utilized to identify a deformity 592-1 . . . 592-N on a vehicle 590 according to the present disclosure. The vehicle lighting apparatus 500 may be a same or similar vehicle apparatus to the examples of vehicle lighting apparatuses described with respect to FIG. 1, FIG. 2, and FIG. 3. The perspective view may include a perspective view of an example of the performance of the method 480 described in FIG. 4.

The vehicle lighting apparatus 500 may be positioned on or near a vehicle 590. The vehicle 590 may include a motor vehicle such as an automobile. The vehicle lighting apparatus 500 may be positioned such that the light emitted by the vehicle lighting apparatus 500 when illuminated is emitted at a panel (e.g., such as the hood panel) of the vehicle 590. As such, when illuminated, an image of the vehicle lighting apparatus 500 and/or an illumination pattern produced by the vehicle lighting apparatus 500 may be present on the surface of the vehicle 590.

The repairer may inspect the panel of the vehicle 590 that is illuminated by the vehicle lighting apparatus 500 for deformities 592-1 . . . 592-N. Deformities 592-1 . . . 592-N may include surface deformities such as dents. The repairer may detect the deformities 592-1 . . . 592-N utilizing the refraction and/or reflection of the light emitted from the vehicle lighting apparatus 500. For example, the light emitted from the vehicle lighting apparatus 500 may follow a substantially uniform set of light paths 594-1 . . . 594-N as they exit the vehicle lighting apparatus 500, strike the substantially uniform surface of the panel of the vehicle 590, and are reflected into the environment. However, when the light emitted from the vehicle lighting apparatus 500 exits the vehicle lighting apparatus 500 and encounters a deformity 592-1 . . . 592-N, it may be refracted and/or reflected in along a different light path 596-1 . . . 596-N from the substantially uniform set of light paths 594-1 . . . 594-N.

As a result, the reflected image of the vehicle lighting apparatus 500 and/or an illumination pattern produced by the vehicle lighting apparatus 500 visible on the panel of the vehicle 590 may appear distorted to the repairer at the area of the deformity 592-1 . . . 592-N. Where illumination patterns and/or illumination gradients are present from the vehicle lighting apparatus 500, the pattern will be visibly disrupted and/or the illumination intensity will be visibly different at the portion of the panel where the deformities 592-1 . . . 592-N are located. When utilized for paintless dent repair, the repairer may monitor the progress of the repair and adjust their repair technique to achieve a repaired panel finished product where the reflection of the vehicle lighting apparatus 500 and/or an illumination pattern produced by the vehicle lighting apparatus 500 are returned to uniformity.

In the foregoing detailed description of the present disclosure, reference is made to the accompanying drawings that form a part hereof, and in which is shown by way of illustration how examples of the disclosure may be practiced. These examples are described in sufficient detail to enable those of ordinary skill in the art to practice the examples of this disclosure, and it is to be understood that other examples may be utilized and that process, electrical, and/or structural changes may be made without departing from the scope of the present disclosure. A "plurality of" is intended to refer to more than one of such things.

The figures herein follow a numbering convention in which the first digit corresponds to the drawing figure number and the remaining digits identify an element or component in the drawing. For example, reference numeral 102 may refer to element "02" in FIG. 1. Likewise, reference numeral 202 may refer to element "02" in FIG. 2. Element "02" may be a same or similar element in FIG. 1 and in FIG. 2. Elements shown in the various figures herein can be added, exchanged, and/or eliminated so as to provide a plurality of additional examples of the present disclosure. In addition, the proportion and the relative scale of the elements provided in the figures are intended to illustrate the examples of the present disclosure, and should not be taken in a limiting sense.

What is claimed:

1. A vehicle lighting apparatus, comprising:
a backing panel;
a light guide panel (LGP) layered over the backing panel, wherein the LGP includes a front surface, a rear surface opposite the front surface, and a plurality of side surfaces connecting the front surface with the rear surface;
a light source positioned along a first side surface of the plurality of side surfaces of the LGP; and
a front film layered over the front surface of the LGP, wherein the LGP includes a plurality of refraction elements, wherein the plurality of refraction elements refract light, emitted from the light source, to concentrate the light to be emitted through a first portion of the front surface of the LGP aligned over the plurality of refraction elements adjacent to a second portion of the front surface of the LGP not aligned over the plurality of refraction elements, and wherein a distribution pattern of the refraction elements creates a corresponding pattern of differing light intensities among the first portion and the second portion visible through the front film when illuminated by the light source.

2. The apparatus of claim 1, wherein the refraction elements include a plurality of dot depressions in the rear surface of the LGP that faces the backing panel.

3. The apparatus of claim 1, wherein the distribution pattern of the refraction elements includes a first portion of the LGP panel with the refraction elements and a second portion of the LGP panel without the refraction elements.

4. The apparatus of claim 3, wherein the first portion of the LGP panel and the second portion of the LGP panel form alternating stripes across the rear surface of the LGP that faces the backing panel.

5. The apparatus of claim 3, wherein the corresponding pattern of differing light intensities include alternating stripes of a greater light intensity, corresponding to the first portion of the LGP panel, and stripes of a lesser light intensity, corresponding to the second portion of the LGP panel.

6. The apparatus of claim 1, wherein the backing panel is reflective.

7. The apparatus of claim 1, wherein the front film is a plastic light diffusing panel.

8. The apparatus of claim 1, wherein the LGP is a transparent acrylic panel.

9. A vehicle lighting apparatus, comprising:
a light guide panel (LGP) including a front surface, a rear surface opposite the front surface, and a plurality of side surfaces connecting the front surface with the rear surface;
a powered LED light source positioned along a first side surface of the plurality of side surfaces of the LGP such that a light produced by the LED light source enters the LGP through the first side surface;
a reflector panel positioned against the rear surface of the LGP such that a portion of the light produced by the LED light source that exits the rear surface of the LGP is reflected back into the LGP by the reflector panel;
a plurality of refraction elements in the LGP, wherein the plurality of refraction elements is distributed at a first density across a first portion and a second portion of the LGP and distributed at a second density across a third portion of the LGP separating the first portion and the second portion, wherein the plurality of refraction elements refract the light produced by the LED light source to exit the front surface of the LGP concentrated within an area of the front surface aligned immediately over the plurality of refraction elements; and
a light diffusing panel layered over the front surface of the LGP.

10. The vehicle lighting apparatus of claim 9, comprising a fourth portion of the LGP between the first portion and the third portion, wherein the plurality of refractive elements is distributed at a third density across the fourth portion.

11. The vehicle lighting apparatus of claim 10, wherein the first density of refraction elements is greater than the third density of refraction elements, and wherein the third density of refraction elements is greater than the second density of refractions elements.

12. The vehicle lighting apparatus of claim 10, wherein a density gradient from a greater density of refraction elements to a lesser density of refraction elements is formed from the first portions of the LGP to the third portion of the LGP.

13. The vehicle lighting apparatus of claim 9, wherein the plurality of refraction elements is distributed to project a plurality of stripes through the face of the light diffusing panel when the LED light source is producing the light, wherein a first portion of the plurality of stripes has an illuminated appearance and wherein a second portion of the plurality of stripes has a darkened appearance.

14. The vehicle lighting apparatus of claim 9, comprising a side surface reflector positioned against a face of a second side surface.

15. The vehicle lighting apparatus of claim 9, wherein the light diffusing panel is a translucent colored panel to alter a hue of the light passed through it.

16. The vehicle lighting apparatus of claim 9, wherein the light diffusing panel includes a printed pattern to block a portion of the light passed through it.

17. The vehicle lighting apparatus of claim 9, wherein a face of the first side surface of the LGP and a face of the front surface of the LGP are perpendicular to each other.

18. A method of identifying a dent on a vehicle, comprising:
illuminating a portion of a vehicle with a vehicle lighting apparatus, wherein the vehicle lighting apparatus includes a:
a light guide panel (LGP) including a front surface, a rear surface opposite the front surface, and a plurality of side surfaces connecting the front surface with the rear surface,
a powered light source positioned along a first side surface of the plurality of side surfaces of the LGP such that a light produced by the light source enters the LGP through the first side surface,
a reflector panel positioned against the rear surface of the LGP such that a portion of the light produced by the light source that exits the rear side of the LGP is reflected back into the LGP by the reflector panel,
a plurality of refraction elements in the LGP, wherein the plurality of refraction elements refract the light produced by the light source to exit the front surface of the LGP concentrated within an area of the front surface of the LGP aligned immediately over the plurality of refraction elements, and
a light diffusing panel layered over the front surface of the LGP,
wherein the vehicle lighting apparatus outputs a plurality of alternating bright stripes and dark stripes to illuminate the vehicle, wherein the bright stripes correspond to the area of the front surface of the LGP aligned immediately over the plurality of refraction elements and wherein the dark stripes correspond to an area of the front surface of the LGP not aligned immediately over the plurality of refraction elements;
inspecting the portion of the vehicle utilizing the plurality of alternating bright stripes and dark stripes output by the vehicle lighting module; and
identifying the dent on the vehicle from the inspection.

19. The method of claim 18, wherein the plurality of refraction elements is distributed in alternating stripes of alternating densities across the rear surface of the LGP to produce the output of the plurality of alternating bright stripes and dark stripes when the light source is producing light.

20. The method of claim 17, wherein the light diffusing panel includes alternating opaque stripes and alternating translucent stripes to produce the output of the plurality of alternating bright stripes and dark stripes.

* * * * *